United States Patent [19]

Stephens

[11] Patent Number: 5,690,663
[45] Date of Patent: Nov. 25, 1997

[54] SAFETY TROCAR

[75] Inventor: Randy R. Stephens, Fairfield, Ohio

[73] Assignee: Ethicon Endo-Surgery Inc., Cincinnati, Ohio

[21] Appl. No.: 657,532

[22] Filed: Jun. 4, 1996

Related U.S. Application Data

[63] Continuation of Ser. No. 296,217, Aug. 25, 1994, abandoned.

[51] Int. Cl.⁶ .................................................. A61B 17/34
[52] U.S. Cl. ................................... 606/185; 604/264
[58] Field of Search ............................ 604/164, 264; 606/1, 167, 171–185

[56] References Cited

U.S. PATENT DOCUMENTS

| | | | |
|---|---|---|---|
| 5,263,937 | 11/1993 | Shipp | 604/264 |
| 5,275,583 | 1/1994 | Crainich | 606/184 |
| 5,314,417 | 5/1994 | Stephens et al. | 604/264 |
| 5,350,393 | 9/1994 | Yoon | 606/185 |
| 5,411,515 | 5/1995 | Haber et al. | 606/184 |

*Primary Examiner*—Glenn Dawson
*Attorney, Agent, or Firm*—Paul A. Coletti

[57] ABSTRACT

A safety trocar is provided which includes a spring-loaded shield that shields the cutting tip of the obturator after the obturator penetrates tissue. The distal end of the shield is conical in profile and contains a slot which conforms to the geometry of the cutting tip. The obturator tip contains a knife edge blade which extends the length of the cannula inner diameter. Ideally, the knife is made of an amorphous metal, and may be serrated at its edge. In one embodiment, the knife edge is contacted directly to a portion of the safety shield.

4 Claims, 4 Drawing Sheets

SAFETY TROCAR

This is a continuation of application Ser. No. 08/296,217, filed Aug. 25, 1994 now abandoned.

FIELD OF THE INVENTION

This invention relates to trocars used to puncture tissue for the performance of laparoscopic or arthroscopic surgery and, in particular, to such trocars which employ a safety device to shield the obturator point immediately after the point has perforated tissue.

BACKGROUND OF THE INVENTION

A trocar generally comprises two major components, a trocar tube and an obturator. The trocar tube or cannula is inserted through the skin. Access is gained through to a body cavity so that laparoscopic or arthroscopic surgery may be performed. In order to penetrate the skin, the distal end of the trocar tube is placed against the skin and an obturator is inserted through the tube. By pressing against the proximal end of the obturator the point of the obturator is forced through the skin until the obturator enters the body cavity. At this time, the trocar tube is inserted through the perforation made by the obturator and the obturator is withdrawn, leaving the trocar tube as an accessway to the body cavity.

It has been found that often a great deal of force is required to cause the obturator point to penetrate the skin and underlying tissue. When the point finally breaks through this tissue, resistance to penetration is suddenly removed, and the obturator point can suddenly reach to penetrate internal organs of the body, which may cause lacerations and other injury to the internal organs. To avert this danger to the patient, trocars have been developed which carry a spring-loaded tubular shield within the trocar tube and surrounding the obturator. The distal end of the shield presses against the skin as the obturator point penetrates the body, until the obturator has formed a perforation with a diameter sufficient to allow the safety shield to pass through. At that time the resistance of the tissue to the spring-loaded shield is removed, and the shield will spring forward to extend into the body cavity, surrounding the point of the obturator. The shield thus protects the internal body organs from inadvertent contact with the point of the obturator. A trocar including such a safety shield is described in U.S. Pat. No. 4,535,773, for example.

The tubular shield in such a trocar will, however, require the incision formed by the obturator to extend to a considerable diameter before the resistance of the tissue pressure has been sufficiently decreased to allow the safety shield to spring forward. It is only when the incision attains the diameter of the shield that the shield is fully able to spring into the body cavity. When the obturator employs a long, tapered cutting tip, this tip must extend a significant distance into the body before the incision is sufficiently enlarged to release the safety shield. It would therefore be desirable to provide a safety shield which will spring forward to shield the obturator tip as soon as possible after entry is gained to the body cavity.

In accordance with the principles of Deniega, U.S. Pat. No. 5,066,288, a safety shield for a trocar obturator is provided which exhibits a rounded, bullet-shaped distal end. A slot is formed in this distal end which corresponds to the geometry of the obturator tip, through which the tip extends during perforation of the skin. With this distal end conforming to the geometry of the tip, a smooth transition is provided from the tip to the distal end of the shield, enabling the shield to closely follow the obturator tip through the tissue. The rounded distal end will press against the skin and tissue in close proximity to the periphery of the incision as it is formed, and will aid in the enlargement of the incision to enable the shield to spring forward nearly as soon as entry is gained into the body cavity.

One desirable function of such a trocar is for the obturator to slide smoothly within the trocar tube during both insertion and retraction of the obturator. Opposing this need is the necessity to form the obturator to be nearly the same diameter as the tube, so that the tissue perforation will be the size of the tube. Thus, tolerances are generally tight between the diameter of the obturator and the inside diameter of the trocar tube. A further complication is provided by the valve at the proximal end of the trocar tube, which is needed to seal the proximal end during removal of the obturator when the trocar tube and body cavity are insufflated with gases. The valve, which generally takes the form of a hinged flap or trumpet valve, is spring-loaded to bear against the obturator, thereby assuring that the valve will close automatically upon withdrawal of the obturator from the trocar tube. As the valve bears against the obturator it will frictionally disrupt the entry and withdrawal of the obturator. As a result of these tolerance problems, heretofore there has not been an obturator which corresponds identically to the shaft of the trocar cannula, and wider than the inner dimension of the safety shield in which the obturator slides.

Further patient safety would be provided by preventing the sudden extension of the obturator into the body cavity as the obturator tip fully penetrates the tissue. In accordance with yet another aspect of Deniega '688, means are provided which permit only incremental advancement of the obturator as tissue penetration proceeds. Such incremental advancement is provided by a ratchet or screw mechanism, for instance. Yet, this has not alleviated the problem of having an obturator tip with only minimal exposure past the edge of the safety shield at all positions of the safety shield distal end.

SUMMARY OF THE INVENTION

It is therefore an object of the present invention to provide a trocar with a safety shield such that the cutting edge of the obturator tip of the safety shield corresponds with the inner diameter of the trocar cannula. This improvement would reduce the force to penetrate the abdominal wall with using such trocar.

It is further desirable to form the obturator tip out of any one of the amorphous-type metals which have currently come into use. These amorphous metals such as amorphous steels and the like, have heretofore not been used in the medical industry for tissue piercing purposes, such as in trocar obturator tips.

Further, it is an object of the invention to provide a safety shielded trocar with a conical shape shield. This type of shield provides for ease of tissues spreading, and as well as adapts to be conformable to various types of obturator tips.

In this type of safety shield it is desired to provide a diametral slot. This slot allows passage of the knife edge which causes a diametral slit to be made in the abdominal wall upon puncture. It is believed that such a slit, would tend to improve healing and simulates the cut of a scalpel, rather than the standard triangular point openings as made with standard trocars. It has the added effect of quicker safety shield response time, to cover the obturator tip.

Furthermore, it has been found that trocar obturators with small diameter (5 mm or less), which are merely two sided blades, need an increased mass to better puncture the abdominal wall. It is an object of the invention to provide such mass to the trocar obturator.

These and other objects of the invention are provided in a trocar which comprises an obturator connected to an obturator handle and the obturator having a sharpened tip. This obturator may be inserted into a cannula which is connected to a cannula handle. The cannula itself has an opening with an internal diameter. Also, the device contains a safety shield which is spring-loaded within the obturator handle. The safety shield is capable of covering the obturator tip. The safety shield contains within it an opening through which the obturator tip may pass. Generally, the obturator tip when it extends through the opening abuts the inner diameter of the cannula. Generally, the obturator tip is formed from an amorphous metal and contains a curved profile, forming a knife edge. The knife edge indeed may contain serrations. Also, the safety shield is conical in shape so that it is more readily able to spread tissue and has a slit which has a width extending across the inner diameter of the cannula. In one embodiment the blade is connected to a portion of the safety shield.

In operation, therefore the trocar of the present invention affords easier puncture, more rapid healing, and uses highly accurately shaped metals which allow for the rapid piercing of the abdominal wall. The trocar of this invention is able to be pressed through tissue, and yet will be protected by the covering by the safety shield over the obturator tip. The safety shield attached to the bilateral blade provides the ideal means to puncture tissue. Especially true for smaller size trocars (5 mm or less), the obturators are now made much more readily useful.

It is believed that this invention will be better understood by reference to the attached drawings taken in connection with the Detailed Description of the Invention.

DESCRIPTION OF THE DRAWINGS

FIG. 7a is a combination view of the obturator tip of FIG. 5 covered by the safety shield, while

DETAILED DESCRIPTION OF THE INVENTION

Figure 1:
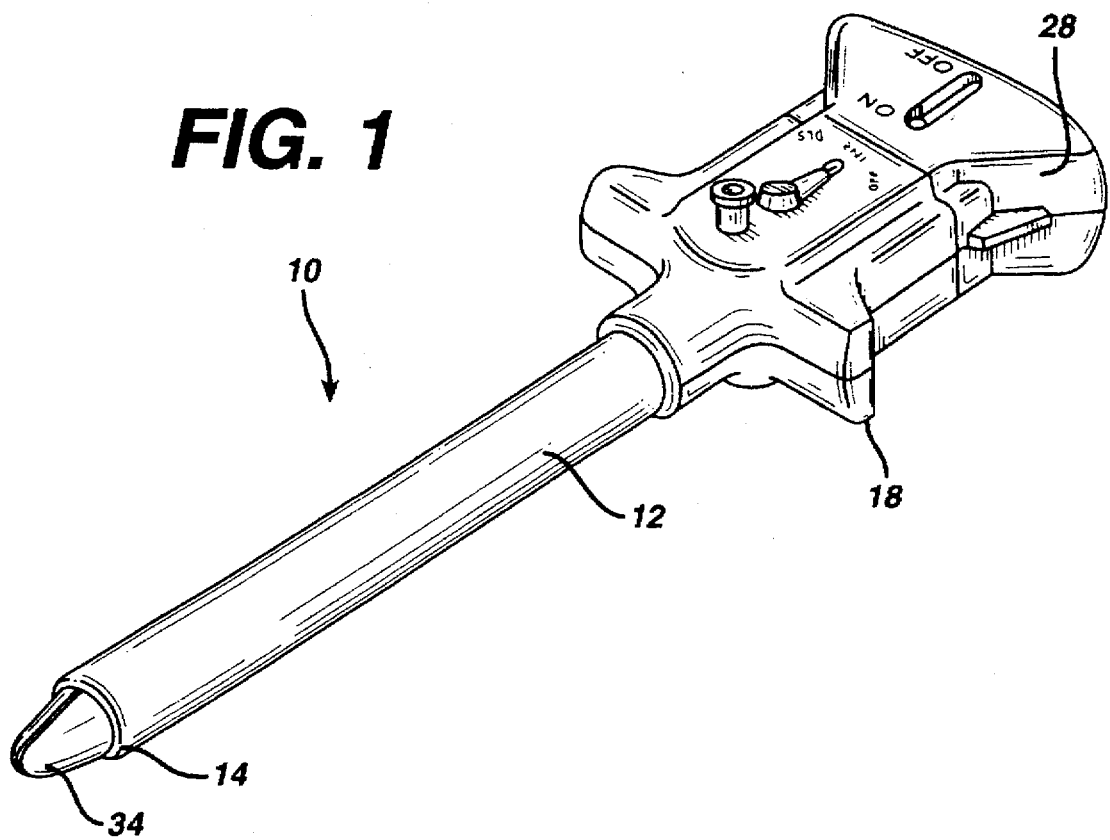
FIG. 1 is a perspective view of a trocar with a conically shaped safety shield.
Figure 8:
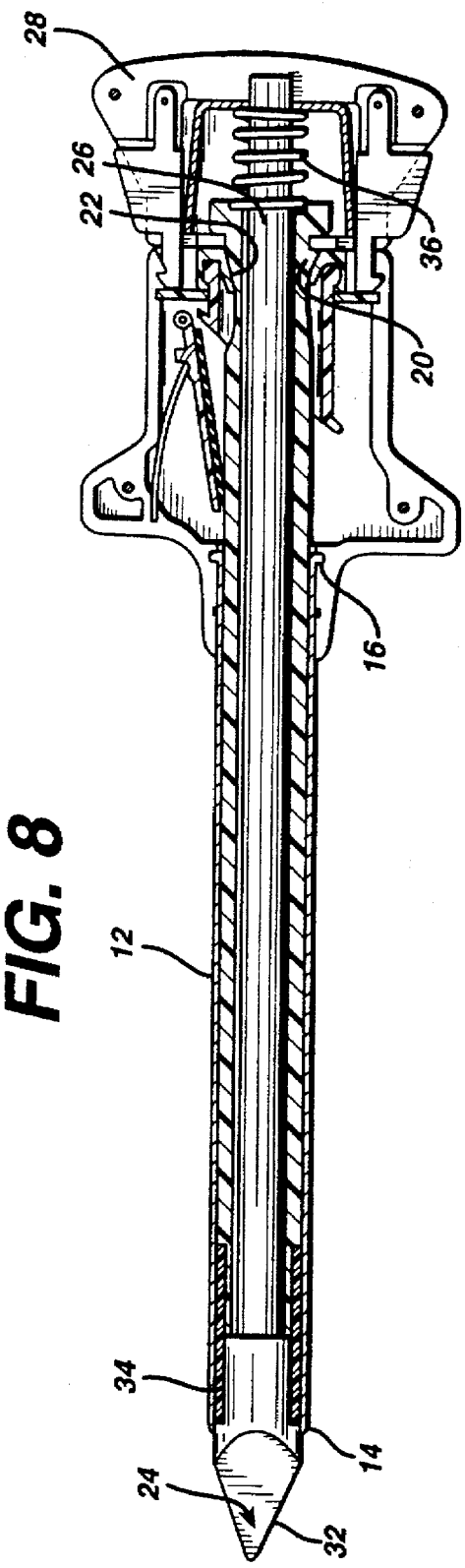
FIG. 8 is a cross-sectional view of the trocar of FIG. 1.

A safety trocar constructed in accordance with the principles of the present invention is shown in FIGS. 1 and 8. The trocar 10 includes a trocar tube or cannula 12 having an open distal end 14 and open flanged proximal end 16. The proximal end 16 is mounted in a trocar handle 18. There is an aperture 20 at the proximal end 16 of the trocar handle 18 which is surrounded by a gasket ring 22.

An obturator 24 is slidably and removably located within the trocar cannula 12 and is inserted into the handle 18 and trocar cannula 12 by way of the aperture 20 in the trocar cannula handle 18. Obturator 24 may reciprocate into obturator handle 28 in a slidable fashion, or conversely may rotate within handle 28. At obturator proximal end 26 is an obturator handle 28, and the distal end 30 of the obturator 24 is sharpened as a knife edge 32. The safety trocar 10 of the FIGS. 1 and 8 is used to puncture a hole in soft tissue by placing the distal end 14 of the trocar cannula 12 against tissue and pressing against the obturator handle 28. As pressure is exerted against the obturator handle 28, the safety shield 34 begins to compress the spring 36 inside the obturator handle 28, and the shield 34 retracts into the handle 28. This retraction exposes the obturator knife edge 32, which punctures the tissue.

Figure 7A:
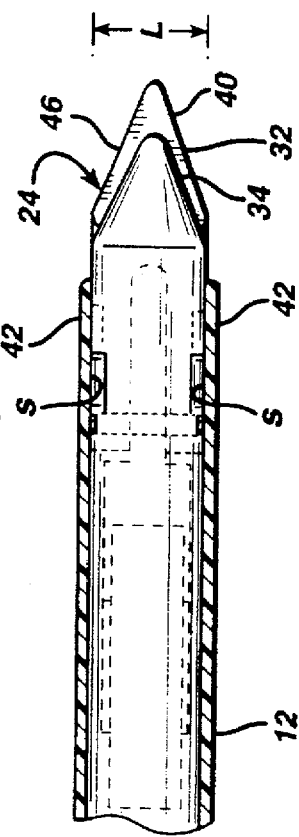
Figure 7B:
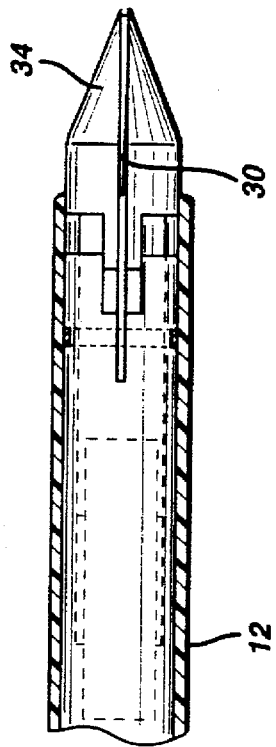
FIG. 7b is a view of the safety shield allowing the exposure of the obturator tip of the invention.

FIG. 7b shows the shield 34 is fully compressed (within the obturator handle 28) and the obturator knife edge 32 is fully exposed beyond the distal end of the safety shield 34 and trocar cannula 12. When the obturator knife edge 32 breaks through the inner surface of the tissue, the spring-loaded safety shield 34 springs forward around the obturator distal end 30, shielding the obturator knife edge 32, to prevent inadvertent contact of the edge 32 with internal organs of the body inside the tissue being punctured.

Figure 2:
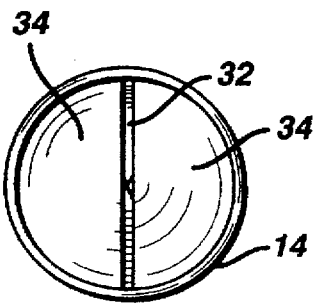
FIG. 2 is a bottom view of the trocar of FIG. 1.
Figure 5:
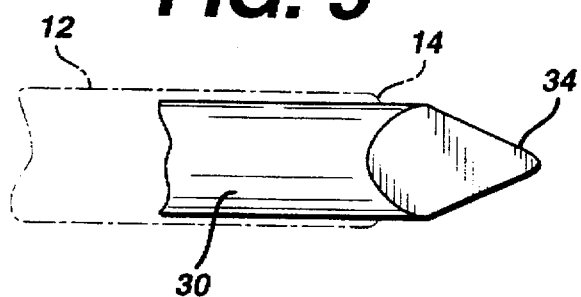
FIG. 5 is a side view of the obturator tip of the invention taken alone without the safety shield covering it.

Operation of the trocar with the safety shield of this invention is shown in FIGS. 1, 2 and 7b. FIG. 1 is a perspective view of the trocar 10 with the trocar cannula 12 held with inside trocar handle 18 so that the end of the safety shield 34 extends from the distal end 14 of the trocar cannula 12. An end view of the distal end 12 of the cannula is shown in FIG. 2. FIG. 5 is a view of the obturator 24 alone without the shield 34 over it. FIG. 7b is view of the distal end of the instrument of FIG. 1, with the knife edge 32 of the obturator 24 extended and the obturator distal end 30 moved apart from the safety shield 34. In FIG. 7a, the obturator distal end 30 is shown covered by the safety shield 34 of FIG. 7b.

Figure 3:
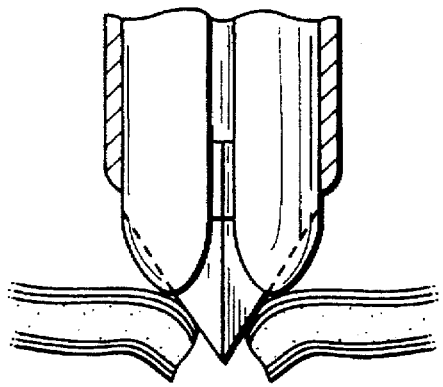
FIG. 3 demonstrates the capability of prior art obturator tips as to piercing tissue.
Figure 4:
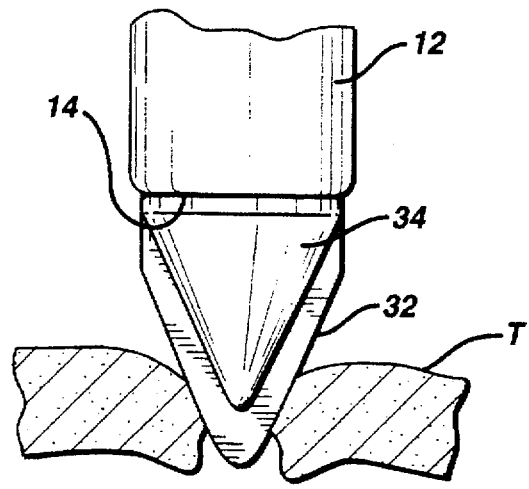
FIG. 4 illustrates the obturator tip of the present invention piercing tissue.

While this invention has been described in general, various aspects of the device will now be described more in particular. First, it is necessary to look at the obturator distal end 30 as seen in FIGS. 1, 5, 7a and 7b, and 8. This obturator distal end 30 is generally a diametrally shaped knife edge 32. It contains two planar faces 40 which form the sharpened knife edge 32. The diametrally shaped knife edge 32 extends across the entire length L of the inner diameter of the trocar cannula. In this way, the dimensions of the knife edge 32 enable it to be placed flush against the sides S of the trocar cannula 12. This configuration lowers the force necessary to puncture and penetrate tissue. This is true because with such a knife edge 32, the obturator 24 is able to move adjacent the edges 42 of the trocar cannula 12. Therefore, when the tissue T encounters the trocar cannula 12, there is no further spreading of tissue by the cannula 12. This is in contrast with the trocar of the prior art inventions, (as seen in FIG. 3) tissue cannot be caught between the obturator tip and the safety shield.

It should be noted that knife edge 32 should be taken in conjunction with the safety shield 34 of this invention. It will be noticed that the safety shield 34 is conical in shape. This conically-shaped safety shield, generally made of a plastic, will cause the tissue to spread in a very gradual fashion. Of course, the conical shape may be steeper or shallower with respect to the diameter of cannula 12 dependent on the desired severity of puncture. Naturally, a steeper (longer) conical height will provide smoother puncture. In addition, because the safety shield 34 also abuts the internal diameter of the trocar cannula 12, the safety shield 34 also is able to perform better spreading of the tissue.

It will be seen that the knife edge 32 at its bottom as in FIG. 2 forms a rather long diametral slits. This is different than the traditional triangular shaped cuts made by traditional trocars. This cut is more like the cut of scalpel. In this way, tissue healing will be promoted in that less tissue must be brought together at the skin surface. Also, because the tissue is very readily pierced, this formulation of the knife edge 32 and safety shield 36 enables easier force to pierce during piercing.

Figure 6A:
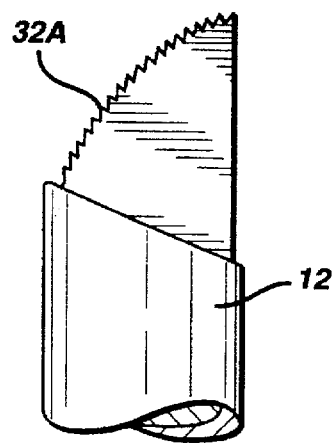
FIGS. 6a and 6b are alternate views of an obturator tip of this invention.
Figure 6B:
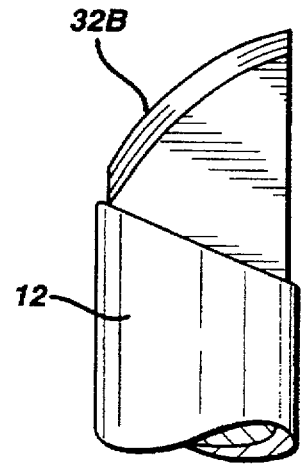

As seen in FIGS. 6a and 6b, there are shaped two alternate forms of knife edges, 32A, 32B, both based on a dimetral slit design. In one knife edge 32A contains a serrated edge. This serrated edge 32A is able to cut through tissue with a much greater ease. Of course, the serrated edge 32A creates greater surface area contact in tissue, but does not detract from the size or shape of the knife edge.

Alternately, in FIG. 6b, there is described a tip 32B with a generally scalpel shape. This scalpel shape used in conjunction with a safety shield compatible with it allows the user to pierce the tissue using the same holding position as using a scalpel. This can be particularly useful for endoscopic applications of such a knife edge 32B. These knife edges may be placed at an angular orientation to form a cutting shape between 10° and 60° with the sides of the cannula 12.

In fact, the obturator 24 of this invention is also useful as a piercing instrument. That is, because the obturator 24 of the present design is useful to pierce tissue, much like a scalpel, this obturator 24 may be borrowed to be used endoscopically down a long trocar cannula in order to cut tissue internally. Of course, the safety shield 34 of this mechanism must be adapted so that it is able to be covered only when desired and not automatically after piercing through tissue.

The obturator 32 of this invention maybe formed from an amorphous metal, much like that described in Ser. No. 786,752, now U.S. Pat. No. 5,314,417 assigned to a common assignee as this invention. This amorphous metal can be very highly shaped and refined to very small dimensions, such as about 0.001" or less. In this way, the knife edge of this mechanism is very readily adapted to pierced tissue. Also, because the amorphous metals may be formed as serrated edges as in FIG. 6a, we are able to use such a knife edge to perform useful endoscopic functions. Nonetheless, other materials are also available, such as ceramics and the typical stainless steel, from which to form the knife edge.

Figure 9:
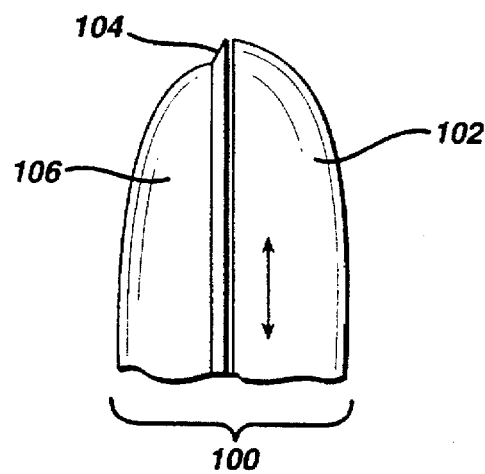
FIGS. 9 and 9A are perspective views of a modified combination blade and safety shield.
Figure 9A:
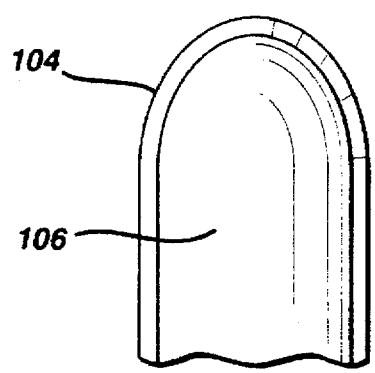
Figure 10:
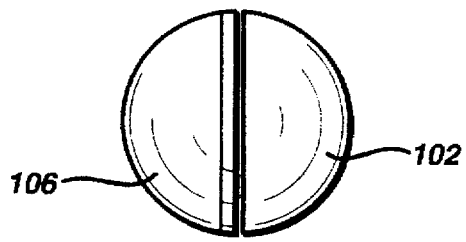
FIG. 10 is a top view of FIG. 9.
Figure 11:
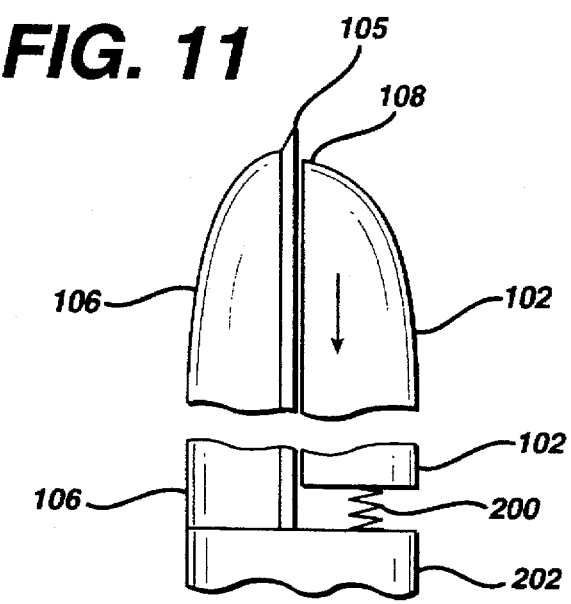
FIG. 11 is a view of FIG. 9 in the cutting position.

A modified combination safety shield and blade is described in FIGS. 9, 10 and 11. As seen in the figures, attached to the distal end of the obturator shaft 202 which is inserted into the trocar cannula (identified as item 12 in FIG. 1) is a stationary safety shield 106 and a spring-loaded shield portion 102. At the distal end of the shield 106 is a sharpened stainless steel semicircular cutting blade 104 similar to the cutting blades shown in FIGS. 1 to 8. The stationary safety shield and blade combination (as seen in FIG. 10) encompasses half of the trocar cannula 12 cross-section such that the blade 104 extends diametrically along the circumference of the trocar cannula 12. Opposite to the stationary portion of the safety shield 106 is the spring loaded shield portion 102. The proximal end of the spring-loaded shield portion 102 is connected to the distal end of shaft 202 by a spring 200. The distal end 108 of this movable portion 102 extends to the tip of the blade 104 on the stationary portion 106. Thus, when this movable portion 106 is in its distalmost position, and locked thereto, by known conventional locking means (also not shown), the blade 104 is protected from cutting tissue. On the other hand, when the movable shield portion is unlocked, the shield 102 is able to retract proximally into the cannula. In this fashion, the blade 104 becomes exposed and blade tip 105 is free to cut tissue. When pressure against the movable safety shield portion 102 is removed, the movable shield 102 returns to its fully extended position and locks in that position. At that point, the blade no longer may cut tissue.

This embodiment is particularly suited for small (5 mm or less) trocars, as the blade 104, which is quite thin (less than 0.005"), is reinforced by the stationary shield 106. This mass added to blade 104 provides a useful platform on which to cut tissue.

This new trocar presents many improved uses. There are also equivalents that can be discerned from the description of this invention. Such equivalents are intended to be covered by the scope of this invention as to be derived from the attached claims.

What is claimed is:

1. A trocar obturator comprising:
    an elongated shaft having a distal end and a proximal end;
    a blade with a distal cutting end and a proximal end, said blade proximal end attached to the distal end of said shaft;
    a stationary shield portion affixed to said blade, said stationary shield portion having a distal end and a proximal end;
    a movable shield portion attached by a spring to the distal end of said shaft, said movable shield portion slidable with respect to said stationary shield portion and said blade, such that said movable shield portion may be retracted proximally from the distal cutting end of said blade to allow cutting by said blade;
    wherein said blade distal cutting end extends distally from said stationary shield distal end, and said blade distal cutting end is generally semicircular in shape.

2. The obturator of claim 1 wherein said trocar obturator is part of a trocar system comprising at least a cannula into which said obturator is insertable.

3. The obturator of claim 2 wherein said cannula is 5 mm or less in diameter.

4. A trocar obturator comprising:
    an elongated shaft having a distal end and a proximal end;
    a blade with a distal cutting end and a proximal end, said blade proximal end attached to the distal end of said shaft;
    a stationary shield portion affixed to said blade, said stationary shield portion having a distal end and a proximal end;
    a movable shield portion attached by a spring to the distal end of said shaft, said movable shield portion slidable with respect to said stationary shield portion and said blade, such that said movable shield portion may be retracted proximally from the distal cutting end of said blade to allow cutting by said blade;
    wherein said blade distal cutting end extends distally from said stationary shield distal end, and said blade distal cutting end is generally semicircular in shape; and
    further comprising locking means to lock said movable shield portion in a locked position with respect to said stationary shield portion and said blade so that the respective distal ends of said movable shield portion and said blade are coextensive in said locked position.

* * * * *